United States Patent [19]
Zoeller et al.

[11] Patent Number: 6,160,163
[45] Date of Patent: Dec. 12, 2000

[54] METHOD FOR THE VAPOR-PHASE CARBONYLATION OF LOWER ALIPHATIC ALCOHOLS USING A SUPPORTED PLATINUM CATALYST AND HALIDE PROMOTER

[75] Inventors: Joseph Robert Zoeller; Andy Hugh Singleton; Gerald Charles Tustin, all of Kingsport; Donald Lee Carver, Church Hill, all of Tenn.

[73] Assignee: Eastman Chemical Company, Kingsport, Tenn.

[21] Appl. No.: 09/250,957

[22] Filed: Feb. 16, 1999

[51] Int. Cl.⁷ .......................... C07C 67/36; C07C 51/12
[52] U.S. Cl. ..................... 560/207; 562/517; 562/519; 562/607
[58] Field of Search ................. 560/207; 562/517, 562/519, 607

[56] References Cited

U.S. PATENT DOCUMENTS

| | | |
|---|---|---|
| 3,689,533 | 9/1972 | Schultz . |
| 3,717,670 | 2/1973 | Schultz . |
| 3,772,380 | 11/1973 | Paulik et al. . |
| 4,110,359 | 8/1978 | Marion . |
| 4,417,077 | 11/1983 | Drago et al. . |
| 4,612,387 | 9/1986 | Feitler . |
| 4,767,574 | 8/1988 | Hanes et al. . |
| 4,776,987 | 10/1988 | Luft et al. . |
| 4,845,163 | 7/1989 | Panster et al. . |
| 4,918,218 | 4/1990 | Mueller et al. . |
| 5,144,068 | 9/1992 | Smith et al. . |
| 5,185,462 | 2/1993 | Evans et al. . |
| 5,218,140 | 6/1993 | Wegman . |
| 5,258,549 | 11/1993 | Pimblett . |
| 5,488,143 | 1/1996 | Uhm et al. . |
| 5,510,524 | 4/1996 | Garland et al. . |
| 5,900,505 | 5/1999 | Tustin et al. . |

FOREIGN PATENT DOCUMENTS

| | | |
|---|---|---|
| 0 120 631 A1 | 10/1984 | European Pat. Off. . |
| 0 130 058 A1 | 1/1985 | European Pat. Off. . |
| 0 461 802 A2 | 12/1991 | European Pat. Off. . |
| 0 596 632 A1 | 5/1994 | European Pat. Off. . |
| 0 752 406 A1 | 1/1997 | European Pat. Off. . |
| 0 759 419 A1 | 2/1997 | European Pat. Off. . |
| 306 863 | 5/1973 | United Kingdom . |

OTHER PUBLICATIONS

J. Yang, A. Haynes and P. Maitilis, "The carbonylation of methyl iodide and methanol to methyl acetate catalysed by palladium and platinum iodides", *Chemical Communication*, No. 2 (Jan. 21, 1999), pp. 179–180, Cambridge, UK.

K. M. Webber, B. C. Gates and W. Drenth, "Design and Synthesis of a Solid Bifunctional Polymer Catalyst for Methanol Carbonylation", *Journal of Molecular Catalysis*, 3 (1997/78) pp. 1–9, Netherlands.

A. Krzywicki and M. Marczewski, "Formation and Evolution of the Active Site for Methanol Carbonylation on Oxide Catalysts Containing $RhCl_3$", *Journal of Molecular Catalysis*, 6(1979) pp. 431–440, Netherlands.

K. Fujimoto, J. Mazaki, K. Omata and H. Tominaga, "Promotion Effect of Hydrogen on Vapor Phase Carbonylation of Methanol Over Nickel on Active Carbon Catalyst", *Chemistry Letters*, (1987) pp. 895–898, Japan.

H. E. Maneck, D. Gutschick, I. Burkardt, B. Luecke, H. Miessner, and U. Wolf, "Heterogeneous Carbonylation of Methanol on Rhodium Introduced Into Faujasite–Type Zeolites", *Catalysis Today*, 3 (1988) pp. 421–429, Netherlands.

P. Gelin, C. Naccache, and Y. Taarit, "Coordination Chemistry of Rhodium and Iridium in Constrained Zeolite Cavities: Methanol Carbonylation", *Pure & Appl. Chem.*, vol. 8, No. 8, (1988) pp. 1315–1320, Great Britain.

H. Yagita, K. Omata, H. Tominaga and K. Fujimoto, "Vapor– phase Carbonylation of Methanol Over Lead on Active Carbon Catalyst", *Catalysis Letters*, 2 (1989) pp. 145–148, Germany.

H. Yagita and K. Jujimoto, "Redox Cycle of Metal–on–Active Carbon Catalyst in the Vapor Phase Carbonylation of Methanol", *Journal of Molecular Catalyst*, 69 (1991) pp. 191–197, Netherlands.

K. Jujimoto, S. Bischoff, K. Omata and H. Yagita, "Hydrogen Effects on Nickel–Catalyzed Vapor–Phase Methanol Carbonylation", *Journal of Catalysis*, 133 (1992) pp. 370–382.

M. J. Howard, M. D. Jones, M. S. Roberts and S. A. Taylor, "$C_1$ to Acetyls: Catalysis and Process", *Catalysis Today*, 18 (1993) pp. 325–354, Amsterdam.

T. Liu and S. Chiu, "Promoting Effect of Tin on Ni/C Catalyst for Methanol Carbonylation", *Ind. Eng. Chem. Res.*, 33 (1994) pp. 488–492, USA.

*Primary Examiner*—James O. Wilson
*Assistant Examiner*—Robert W. Deemie
*Attorney, Agent, or Firm*—Matthew Smith; Harry Gwinnell

[57] ABSTRACT

A method for the vapor-phase carbonylation of lower alkyl alcohols to esters and optionally, carboxylic acids using a catalyst having a platinum on a solid support material as a first component and a vaporous halide as a second component. Desirably, the catalyst includes platinum on an activated carbon support and the vaporous halide is selected from hydrogen halides, alkyl halides and aryl halides having up to 12 carbon atoms, and mixtures thereof.

15 Claims, No Drawings

METHOD FOR THE VAPOR-PHASE CARBONYLATION OF LOWER ALIPHATIC ALCOHOLS USING A SUPPORTED PLATINUM CATALYST AND HALIDE PROMOTER

FIELD OF THE INVENTION

The present invention relates to a method for the vapor phase carbonylation of alkyl alcohols, ethers, esters and ester-alcohol mixtures to produce esters and carboxylic acids and particularly, the carbonylation of methanol to produce acetic acid and methyl acetate. More particularly, the present invention relates to the vapor-phase carbonylation of methanol to produce acetic acid and methyl acetate using a catalyst which includes a solid component having platinum associated with a solid support material and a vaporous halide component.

BACKGROUND OF THE INVENTION

Lower carboxylic acids and esters such as acetic acid and methyl acetate have been known as industrial chemicals for many years. Acetic acid is used in the manufacture of a variety of intermediary and end-products. For example, an important derivative is vinyl acetate which can be used as monomer or co-monomer for a variety of polymers. Acetic acid itself is used as a solvent in the production of terephthalic acid, which is widely used in the container industry, and particularly in the formation of PET beverage containers.

There has been considerable research activity in the use of metal catalysts for the carbonylation of lower alkyl alcohols, such as methanol, and ethers to their corresponding carboxylic acids and esters, as illustrated in equations 1–3 below:

$$ROH + CO \rightarrow RCOOH \tag{1}$$

$$2ROH + CO \rightarrow RCOOR + water \tag{2}$$

$$ROR' + CO \rightarrow RCOOR \tag{3}$$

Carbonylation of methanol is a well known reaction and is typically carried out in the liquid phase with a catalyst. A thorough review of these commercial processes and other approaches to accomplishing the formation of acetyl from a single carbon source is described by Howard et al. in *Catalysis Today*, 18, 325–254 (1993). Generally, the liquid phase carbonylation reactions for the preparation of acetic acid using methanol are performed using homogeneous catalyst systems comprising a Group VIII metal and iodine or an iodine-containing compound such as hydrogen iodide and/or methyl iodide. Rhodium is the most common Group VIII metal catalyst and methyl iodide is the most common promoter. These reactions are conducted in the presence of water to prevent precipitation of the catalyst.

U.S. Pat. No. 5,144,068 describes the inclusion of lithium in the catalyst system which allows the use of less water in the Rh-I homogeneous process. Iridium also is an active catalyst for methanol carbonylation reactions but normally provides reaction rates lower than those offered by rhodium catalysts when used under otherwise similar conditions.

U.S. Pat. No. 5,510,524 teaches that the addition of rhenium improves the rate and stability of both the Ir-I and Rh-I homogeneous catalyst systems.

European Patent Application EP 0 752 406 A1 teaches that ruthenium, osmium, rhenium, zinc, cadmium, mercury, gallium, indium, or tungsten improve the rate and stability of the liquid phase Ir-I catalyst system. Generally, the homogeneous carbonylation processes presently being used to prepare acetic acid provide relatively high production rates and selectivity. However, heterogeneous catalysts offer the potential advantages of easier product separation, lower cost materials of construction, facile recycle, and even higher rates.

Schultz, in U.S. Pat. No. 3,689,533, discloses using a supported rhodium heterogeneous catalyst for the carbonylation of alcohols to form carboxylic acids in a vapor phase reaction. Schultz further discloses the presence of a halide promoter.

Schultz in U.S. Pat. No. 3,717,670 describes a similar supported rhodium catalyst in combination with promoters selected from Groups IB, IIIB, IVB, VB, VIB, VIII, lanthanide and actinide elements of the Periodic Table.

Uhm, in U.S. Pat. No. 5,488,143, describes the use of alkali, alkaline earth or transition metals as promoters for supported rhodium for the halide-promoted, vapor phase methanol carbonylation reaction. Pimblett, in U.S. Pat. No. 5,258,549, teaches that the combination of rhodium and nickel on a carbon support is more active than either metal by itself.

In addition to the use of iridium as a homogeneous alcohol carbonylation catalyst, Paulik et al., in U.S. Pat. No. 3,772,380, describe the use of iridium on an inert support as a catalyst in the vapor phase, halogen-promoted, heterogeneous alcohol carbonylation process.

European Patent Applications EP 0 120 631 A1 and EP 0 461 802 A2 describe the use of special carbons as supports for single transition metal component carbonylation catalysts.

European Patent Application EP 0 759 419 A1 pertains to a process for the carbonylation of an alcohol and/or a reactive derivative thereof.

EP 0 759 419 A1 discloses a carbonylation process comprising a first carbonylation reactor wherein an alcohol is carbonylated in the liquid phase in the presence of a homogeneous catalyst system and the off gas from this first reactor is then mixed with additional alcohol and fed to a second reactor containing a supported catalyst. The homogeneous catalyst system utilized in the first reactor comprises a halogen component and a Group VIII metal selected from rhodium and iridium. When the Group VIII metal is iridium, the homogeneous catalyst system also may contain an optional co-promoter selected from the group consisting of ruthenium, osmium, rhenium, cadmium, mercury, zinc, indium and gallium. The supported catalyst employed in the second reactor comprises a Group VIII metal selected from the group consisting of iridium, rhodium, and nickel, and an optional metal promoter on a carbon support. The optional metal promoter may be iron, nickel, lithium and cobalt. The conditions within the second carbonylation reactor zone are such that mixed vapor and liquid phases are present in the second reactor. The presence of a liquid phase component in the second reactor inevitably leads to leaching of the active metals from the supported catalyst which, in turn, results in a substantial decrease in the activity of the catalyst.

The literature contains several reports of the use of rhodium-containing zeolites as vapor phase alcohol carbonylation catalysts at one bar pressure in the presence of halide promoters. The lead references on this type of catalyst are presented by Maneck et al. in *Catalysis Today*, 3, 421–429 (1988),. Gelin et al., in *Pure & Appl. Chem.*, Vol 60, No. 8, 1315–1320 (1988), provide examples of the use of rhodium or iridium contained in zeolite as catalysts for the vapor phase carbonylation of methanol in the presence of halide promoter. Krzywicki et al., in *Journal of Molecular Catalysis*, 6, 431–440 (1979), describe the use of silica, alumina, silica-alumina and titanium dioxide as supports for rhodium in the halide-promoted vapor phase carbonylation of methanol, but these supports are generally not as efficient as carbon. Luft et al., in U.S. Pat. No. 4,776,987 and in related disclosures, describe the use of chelating ligands chemically attached to various supports as a means to attach Group VIII metals to a heterogeneous catalyst for the halide-promoted vapor phase carbonylation of ethers or esters to carboxylic anhydrides.

Evans et al., in U.S. Pat. No. 5,185,462, describe heterogeneous catalysts for halide-promoted vapor phase methanol carbonylation based on noble metals attached to nitrogen or phosphorus ligands attached to an oxide support.

Panster et al., in U.S. Pat. No. 4,845,163, describe the use of rhodium-containing organopolysiloxane-ammonium compounds as heterogeneous catalysts for the halide-promoted liquid phase carbonylation of alcohols.

Drago et al., in U.S. Pat. No. 4,417,077, describe the use of anion exchange resins bonded to anionic forms of a single transition metal as catalysts for a number of carbonylation reactions including the halide-promoted carbonylation of methanol. Although supported ligands and anion exchange resins may be of some use for immobilizing metals in liquid phase carbonylation reactions, in general, the use of supported ligands and anion exchange resins offer no advantage in the vapor phase carbonylation of alcohols compared to the use of the carbon as a support for the active metal component.

Nickel on activated carbon has been studied as a heterogeneous catalyst for the halide-promoted vapor phase carbonylation of methanol. Relevant references to the nickel-on-carbon catalyst systems are provided by Fujimoto et al. in *Chemistry Letters* 895–898, (1987). Moreover, Fujimoto et al. in *Journal of Catalysis*, 133, 370–382 (1992) observed increased rates when hydrogen is added to the feed mixture. Liu et al., in *Ind. Eng. Chem. Res.*, 33 488–492, (1994), report that tin enhances the activity of the nickel-on-carbon catalyst. Mueller et al., in U.S. Pat. No. 4,918,218, disclose the addition of palladium and optionally copper to supported nickel catalysts for the halide-promoted carbonylation of methanol. In general the rates of reaction provided by nickel-based catalysts are lower than those provided by the analogous rhodium-based catalysts when operated under similar conditions.

Other single metals supported on carbon have been reported by Fujimoto et al. in *Catalysis Letters*, 2, 145–148 (1989) to have limited activity in the halide-promoted vapor phase carbonylation of methanol. The most active of these metals is Sn. Following Sn in order of decreasing activity are Pb, Mn, Mo, Cu, Cd, Cr, Re, V, Se, W, Ge and Ga. None of these other single metal catalysts are nearly as active as those based on Rh, Ir, Ni or the catalyst of the present invention.

Yagita and Fujimoto in *Journal of Molecular Catalysis*, 69, 191–197 (1991) examined the role of activated carbon in a metal supported catalyst and observed that the carbonylation activities of Group VIII metals supported on activated carbon are ordered by the affinities between the metal and the halogen.

A number of solid materials have been reported to catalyze the carbonylation of methanol without the addition of the halide promoter. Gates et al., in *Journal of Molecular Catalysis*, 3, 1–9 (1977/78) describe a catalyst containing rhodium attached to polymer bound polychlorinated thiophenol for the liquid phase carbonylation of methanol.

Current, in European Patent Application EP 0 130 058 A1, describes the use of sulfided nickel containing optional molybdenum as a heterogeneous catalyst for the conversion of ethers, hydrogen and carbon monoxide into homologous esters and alcohols.

Smith et al., in European Patent Application EP 0 596 632 A1, describe the use of mordenite zeolite containing Cu, Ni, Ir, Rh, or Co as catalysts for the halide-free carbonylation of alcohols. Feitler, in U.S. Pat. No. 4,612,387, describes the use of certain zeolites containing no transition metals as catalysts for the halide-free carbonylation of alcohols and other compounds in the vapor phase.

U.S. Pat. No. 5,218,140, describes a vapor phase process for converting alcohols and ethers to carboxylic acids and esters by the carbonylation of alcohols and ethers with carbon monoxide in the presence of a metal ion exchanged heteropoly acid supported on an inert support. The catalyst used in the reaction includes a polyoxometallate anion in which the metal is at least one of a Group V(a) and VI(a) is complexed with at least one Group VIII cation such as Fe, Ru, Os, Co, Rh, Ir, Ni, Pd or Pt as catalysts for the halide-free carbonylation of alcohols and other compounds in the vapor phase.

The present invention for the vapor-phase carbonylation of alkyl alcohols, ethers, esters and ester-alcohol mixtures to produce esters and carboxylic acids and particularly, the carbonylation of methanol to produce acetic acid and methyl acetate represents the first demonstration of a method using a catalyst having platinum as the sole active metal component in the heterogeneous catalyst prior art. The use of platinum as a carbonylation catalyst would be beneficial since platinum compounds are both less volatile and less soluble relative to other active catalysts, such as Ir and Rh, and therefore are less likely to be removed from the catalyst support during operation of the carbonylation process.

SUMMARY OF THE INVENTION

Briefly, the present invention provides a method for vapor-phase carbonylation for producing esters and carboxylic acids from reactants comprising lower alkyl alcohols, ethers, esters, and mixtures of ester-alcohols. The method includes contacting the reactants with a catalyst having a solid first component which includes platinum on a solid support material and a halide vaporous second component.

It is an object of the invention to provide a method for the carbonylation of lower alkyl alcohols, esters, ethers and ester-alcohol mixtures to produce esters and carboxylic acids. More particularly, it is an object of the present invention to provide a method for vapor-phase carbonylation of lower alkyl alcohols, ethers, esters and ester-alcohol mixtures to produce carboxylic acids and esters, and particularly acetic acid and methyl acetate.

It is another object of the present invention to provide a method for the vapor-phase carbonylation of methanol using a heterogeneous catalyst having platinum associated with a solid support and a vapor component.

It is another object of the invention to provide a process in which the catalyst is maintained in a solid phase to reduce or eliminate the handling losses of the catalyst.

It is another object of the invention to provide a vapor phase carbonylation process for the production of acetic acid and methyl acetate which utilizes a more stable catalyst and reduces the need for catalyst recovery and recycle as well as solvent recovery.

These and other objects and advantages of the invention will become apparent to those skilled in the art from the accompanying detailed description.

DETAILED DESCRIPTION OF THE INVENTION

A vapor-phase carbonylation method for the continuous production of carboxylic acids and esters is provided by reacting lower alkyl alcohols, ethers and ester-alcohol mixtures with a catalyst having a solid first component and vapor-phase second component. In a preferred embodiment of the invention, a vapor-phase carbonylation method for the continuous production of acetic acid or methyl acetate is provided. The method or carbonylation process is operated in the vapor state and, therefore, is practiced at temperatures above the dew point of the product mixture, i.e., the temperature at which condensation occurs. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent. In practice, this generally dictates a temperature range of about 100° C. to 500° C., with temperatures in the range of 100° C. to 325° C. being preferred and temperature of about 150° C. to 275° C. being more preferred. Operating in the vapor phase is advantageous since it eliminates catalyst dissolution, i.e., metal leaching from the catalyst support, which occurs in the known heterogeneous processes operating in the presence of liquid compounds.

As with temperature, the useful pressure range is limited by the dew point of the product mixture. However, provided that the reaction is operated at a temperature sufficient to prevent liquefaction of the product effluent, a wide range of pressures may be used, e.g., pressures in the range of about 0.1 to 100 bars absolute. The process preferably is carried out at a pressure in the range of about 1 to 50 bars absolute, most preferably, about 3 to 30 bar absolute.

Suitable feedstock for the carbonylation process include lower alkyl alcohols, ethers, ester-alcohol mixtures and, as more fully discussed below esters, which may be carbonylated in accordance with the present invention. Non-limiting examples include alcohols and ethers in which an aliphatic carbon atom is directly bonded to an oxygen atom of either an alcoholic hydroxyl group in the compound or an ether oxygen in the compound and may further include aromatic moieties. Preferably, the feedstock is one or more lower alkyl alcohols having from 1 to 10 carbon atoms and preferably having from 1 to 6 carbon atoms, alkane polyols having 2 to 6 carbon atoms, alkyl alkylene polyethers having 3 to 20 carbon atoms and alkoxyalkanols having from 3 to 10 carbon atoms. The most preferred reactant is methanol. Although methanol is preferably used in the process and is normally fed as methanol, it can be supplied in the form of a combination of materials which generate methanol. Examples of such combination of materials include (i) methyl acetate and water and (ii) dimethyl ether and water. In the operation of the process, both methyl acetate and dimethyl ether are formed within the reactor and, unless methyl acetate is the desired product, they are recycled with water to the reactor where they are later consumed to form acetic acid. Accordingly, one skilled in the art will further recognize that it is possible to utilize the present invention to produce a carboxylic acid from an ester feed material.

Although the presence of water in the gaseous feed mixture is not essential when using methanol, the presence of some water is desirable to suppress formation of methyl acetate and/or dimethyl ether. When using methanol to generate acetic acid, the molar ratio of water to methanol can be 0:1 to 10:1, but preferably is in the range of 0.01:1 to 1:1. When using an alternative source of methanol such as methyl acetate or dimethyl ether, the amount of water fed usually is increased to account for the mole of water required for hydrolysis of the methanol alternative. Accordingly, when using either methyl acetate or dimethyl ether, the mole ratio of water to ester or ether is in the range of 1:1 to 10:1, but preferably in the range of 1:1 to 3:1. In the preparation of acetic acid, it is apparent that combinations of methanol, methyl ester, and/or dimethyl ether are equivalent, provided the appropriate amount of water is added to hydrolyze the ether or ester to provide the methanol reactant.

When the process is operated to produce methyl acetate, no water should be added and dimethyl ether becomes the preferred feedstock. Further, when methanol is used as the feedstock in the preparation of methyl acetate, it is necessary to remove water. However, the primary utility of the process of the present invention is in the manufacture of acetic acid.

In the practice of the process of the invention, the lower alkyl alcohol, ester, and/or ether in the vapor phase is passed through or over a catalyst having a solid phase first component and a vapor phase second component. The solid phase component of the catalyst includes platinum associated with a substantially inert solid support. The form of platinum used to prepare the catalyst generally is not critical. The solid phase component of the catalyst may be prepared from a wide variety of platinum containing compounds and can be in the form of a salt of a mineral acid halide, such as chloroplatinic acid; trivalent nitrogen compounds such as dichlorodiammine platinum; organic compounds of trivalent phosphorous, such as dichlorobis(triphenylphosphine) platinum; olefins, such as dichloro(1,5-cyclooctadiene) platinum; nitrites, such as dichlorobis(bezonitrile) platinum and oxides of platinum may be used if dissolved in the appropriate medium either alone or in combination. The preferred sources of platinum is one of it chlorides, such as any of the various salts of hexachloroplatinate(IV) or a solution of platinum dichloride in either aqueous HCl of aqueous ammonia.

The amount of platinum, as metal, on the support can vary from about 0.01 weight percent to about 10 weight percent, with from about 0.1 weight percent to about 2 weight percent platinum being preferred.

The solid support useful for acting as a carrier for the platinum consists of a porous solid of such size that it can be employed in fixed or fluidized bed reactors. Typical support materials have a size of from about 400 mesh per inch to about ½ inch. Preferably, the support is carbon, including activated carbon, having a high surface area. Activated carbon is well known in the art and may be derived from coal or peat having a density of from about 0.03 grams/cubic centimeter ($g/cm^3$) to about 2.25 $g/cm^3$. The carbon can have a surface area of from about 200 square meters/gram ($m^2/g$) to about 1200 $m^2/g$. Other solid support materials which may be used in accordance with the present invention include pumice, alumina, silica, silica-alumina, magnesia, diatomaceous earth, bauxite, titania, zirconia, clays, magnesium silicate, silicon carbide, zeolites, and ceramics. The shape of the solid support is not particularly important and can be regular or irregular and include extrudates, rods, balls, broken pieces and the like disposed within the reactor.

The platinum can be associated with the solid support by solubilizing, dispersing or suspending the platinum a suitable solvent or liquid vehicle and contacting the platinum solution, dispersion or suspension with the desired solid support. The liquid is evaporated, i.e. the solid support is dried so that at least a portion of the platinum is associated with the solid support. Drying temperatures can range from about 100° C. to about 600° C. for a period greater than about one second. One skilled in the art will understand that the drying time is dependent upon the temperature, humidity, and solvent used. Generally, lower temperatures require longer heating periods to effectively evaporate the solvent from the solid support.

The catalyst system further includes at least one halide vapor component selected from chlorine, bromine and iodine and preferably, the halide compound is selected from bromine, iodine and mixtures thereof, which are vaporous under vapor-phase carbonylation conditions of temperature and pressure. Suitable halides include hydrogen halides such as hydrogen iodide and gaseous hydriodic acid; alkyl and aryl halides having up to 12 carbon atoms such as, methyl iodide, ethyl iodide, 1-iodopropane, 2-iodobutane, 1-iodobutane, methyl bromide, ethyl bromide, benzyl iodide and mixtures thereof. Desirably, the halide is a hydrogen halide or an alkyl halide having up to 6 carbon atoms. Non-limiting examples of preferred halides include hydrogen iodide, methyl iodide, hydrogen bromide, methyl bromide and mixtures thereof. The halide may also be a molecular halide such as $I_2$, $Br_2$, or $Cl_2$.

The molar ratio of methanol or methanol equivalents to halide present to produce an effective carbonylation ranges from about 1:1 to 10,000:1, with the preferred range being from about 5:1 to about 1000:1.

In a preferred aspect of the invention, the vapor-phase carbonylation catalyst may be used for making acetic acid, methyl acetate or mixtures thereof. The process includes the steps of contacting a gaseous mixture comprising methanol and carbon monoxide with a catalyst system in a carbonylation zone and recovering a gaseous product from the carbonylation zone. The catalyst system includes a solid-phase component comprising platinum deposited on a carbon support and a vapor-phase component comprising at least one halide described above.

Carbon monoxide may be fed to the carbonylation zone either as purified carbon monoxide or as a mixture of hydrogen and carbon monoxide. Although hydrogen is not part of the reaction stoichiometry, hydrogen may be useful in maintaining optimal catalyst activity. The preferred ratio of carbon monoxide to hydrogen generally ranges from about 99:1 to about 2:1, but ranges with even higher hydrogen levels are also likely to be useful.

The present invention is illustrated in greater detail by the specific examples presented below. It is to be understood that these examples are illustrative embodiments and are not intended t be limiting of the invention, but rather are to be construed broadly within the scope and content of the appended claims.

In the examples which follow all of the catalysts were prepared in a similar manner except as specified otherwise.

EXAMPLE 1

A solid supported platinum catalyst was prepared by mixing 569 milligrams (mg) of dihydrogen hexachloroplatinate (chloroplatinic acid) having a platinum assay of 40%, (1.17 mmol of Pt, available from Strem (Dexler Industrial Park, 7 Mulliken Way, Newbury Mass.), in 30 milliliters (ml) of distilled water.

The metal salt solution was added to 20.0 g of 12×40 mesh activated carbon granules contained in an evaporating dish. The granules had a BET surface area in excess of 800 $m^2/g$. The mixture was heated using a steam bath and continuously stirred until it became free flowing at which point the mixture was transferred to a 106 cm long×25 mm (outer diameter) quartz tube. The quartz tube was placed in a three-element electric tube furnace so that the mixture was located substantially in the center of the furnace heat zone. Nitrogen, at a flow rate of 100 standard cubic centimeters per minute, was continuously passed through the catalyst bed while the tube was heated from ambient temperature to 300° C. over a 2 hour period. The temperature was held at about 300° C. for 2 hours and then allowed to naturally cool back to ambient temperature. The catalyst prepared in this manner, designated as Catalyst 1, contained 1.10 weight % platinum and had a density of 0.57 g/ml.

Comparative Catalyst 1

A second catalyst, C-1, was prepared using the same procedure as above except 290 milligrams (mg), (1.18 millimoles, (mmol)) of nickel acetate tetrahydrate was used instead of dihydrogen hexachloroplatinate. The catalyst contained 0.34 weight % Ni.

Comparative Catalyst 2

A third catalyst, C-2, was prepared using the same procedure as above except 207 mg (1.17 mmol) of palladium chloride was used instead of the dihydrogen hexachloroplatinate. An additional 10 ml of concentrated HCl was added to the 30 ml of distilled water to solubilize the palladium chloride. The catalyst contained 0.61 weight % Pd.

Comparative Catalyst 3

A fourth catalyst, C-3, was prepared using the same procedure as above except 418 mg (1.17 mmol) of iridium trichloride hydrate was used instead of the dihydrogen hexachloroplatinate. The catalyst contained 1.10 weight % Ir.

Carbonylation of Methanol

In the examples which follow, the reactor consisted of a clean Hastelloy alloy tubing having dimensions of 800 to 950 mm (31.5 and 37 inch) long and an inside diameter of 6.35 mm (¼ inch). The preheat and carbonylation reaction zones of the reactor were prepared by inserting into the tube a quartz wool pad approximately 410 mm from the top. The quartz wool acted as a support for the catalyst. Adjacent to the quartz wool pad the following materials were added: (1) a 0.7 g bed of fine quartz chips (840 microns); (2) 0.5 g of one of the above described catalysts; and (3) an additional 6 g of fine quartz chips which acted as a heat exchange surface to vaporize the liquid feeds. The top of the tube was attached to an inlet manifold for introducing liquid and gaseous feeds. The remaining lower length of tubing (product recovery section) acted as a condenser and consisted of a vortex cooler which varied in length depending on the original length of tubing employed and was maintained at approximately 0–5° C. during operation.

The gases were fed using Brooks flow controllers and liquids were fed using a high performance liquid chromatography pump. Care was taken not to allow any liquid feeds to contact the solid catalyst materials at any time, including assembly, start-up, and shutdown. The product reservoir tank was placed downstream from the reactor system. The pressure of the reactor was maintained using a Tescom 44-2300 pressure regulator on the outlet side of the reactor system and the temperature of the reaction section was maintained using heating tape on the outside of the tube.

Hydrogen and carbon monoxide were fed to the reactor when the reactor equilibrated at a temperature of about 240° C. and a pressure of 17.2 bara (250 psia). The hydrogen flow rate was maintained at 25 standard cubic centimeters per minute (cc/min). The carbon monoxide flow rate was maintained at 100 cc/min. The reactor was maintained under these conditions for 1 hour or until the temperature and pressure had stabilized, whichever was longer. The high pressure liquid chromatography pump was then started, feeding at a rate of 10–12 g per hour a mixture consisting of 70 weight percent methanol and 30 weight percent methyl iodide. Samples of the liquid product were collected and analyzed as indicated in Table 1 using gas chromatographic techniques known to those skilled in the art.

Carbonylation Example 1

Samples of the product stream were taken as shown below during the methanol carbonylation for Catalyst I. The weight and composition of the each sample are set forth in Table 1. "Time" is the total time of operation of carbonylation as measured from the feeding of methanol until the indicted sample was taken. The values for methyl iodide ("MeI"), methyl acetate ("MeOAc"), methanol ("MeOH") and acetic acid ("HOAc") are weight percent based on the total weight of these compounds in the sample and were obtained using a flame ionization detector.

TABLE 1

| Sample Number | Time (hours) | MeI | MeOAc | MeOH | HOAc | Sample (grams) |
|---|---|---|---|---|---|---|
| 1 | 4.00 | 16.96 | 4.93 | 62.55 | 0.78 | 30.2 |
| 2 | 5.50 | 17.64 | 8.03 | 59 | 1.6 | 23.5 |
| 3 | 8.50 | 18.33 | 17.58 | 46.45 | 5.17 | 24.1 |
| 4 | 12.00 | 18.32 | 17.46 | 46.01 | 5.11 | 48.9 |
| 5 | 16.00 | 16.38 | 16.21 | 53.22 | 3.78 | 70.1 |
| 6 | 19.00 | 16.41 | 16.23 | 53.96 | 3.74 | 28.3 |
| 7 | 24.00 | 14.26 | 26.74 | 35.1 | 10.77 | 20.2 |
| 8 | 27.00 | 19.73 | 36.31 | 7.47 | 19.39 | 30.9 |
| 9 | 28.50 | 16.88 | 27.32 | 37.79 | 4.52 | 26.4 |
| 10 | 32.50 | 20.76 | 35.61 | 5.53 | 21.61 | 48.6 |
| 11 | 34.50 | 20.75 | 35.6 | 5.53 | 21.64 | 22.9 |
| 12 | 40.00 | 12.59 | 11.78 | 65.13 | 2.04 | 70.4 |
| 13 | 43.00 | 12.46 | 11.73 | 65.01 | 2.03 | 22.1 |
| 14 | 48.00 | 15.13 | 22.49 | 42.36 | 7.88 | 49 |
| 15 | 50.00 | 17.14 | 29.76 | 23.07 | 15.83 | 28.5 |

The rate of acetyl production based on the preceding experiment utilizing Catalyst I is set forth in Table 2 below. The Sample Number and Time values correspond to those of Table 1. "Acetyl Produced" represents the quantity, in millimoles, of methyl acetate and acetic acid produced during each increment of Time. Acetyl Produced is calculated from the formula:

Acetyl Produced=(Sample weight (grams))×10×((weight % of MeOAc/74)+(weight % of AcOH/60)).

"Production Rate" is the moles of Acetyl Produced per liter of catalyst volume per hour during each increment of Time (Time Increment), i.e., the time of operation between samples. The formula for determining moles of Acetyl Produced per liter of catalyst volume per hour is determined as follows:

0.57×Acetyl Produced/(0.5×Time Increment)

wherein 0.5 is the grams of catalyst used and 0.57 is the density of the catalyst in g/mL.

TABLE 2

| Sample Number | Acetyl Produced (mmol) | Rate (mol/L-h) |
|---|---|---|
| 1 | 24.0 | 6.9 |
| 2 | 31.8 | 24.1 |
| 3 | 78.0 | 29.6 |
| 4 | 157.0 | 51.1 |
| 5 | 197.7 | 56.4 |
| 6 | 79.7 | 30.3 |
| 7 | 109.3 | 24.9 |
| 8 | 251.5 | 95.6 |
| 9 | 117.4 | 89.2 |
| 10 | 408.9 | 116.5 |
| 11 | 192.8 | 109.9 |
| 12 | 136.0 | 28.2 |
| 13 | 42.5 | 16.2 |
| 14 | 213.3 | 48.6 |
| 15 | 189.8 | 108.2 |

Over the 50 hours of testing, the catalyst produced 2.23 moles of acetyl. This represents a rate of 89 moles of acetyl per kilogram of catalyst per hour (acetyl/$kg_{cat}$-h) or, represented as an hourly space velocity, 45 mol of acetyl/$L_{cat}$-h.

Comparative Carbonylation Examples 1–3

Comparative catalysts, C-1, C-2 and C-3 above were used in the carbonylation of methanol using the same procedure and parameters as described above. The Production Rate, expressed in terms of moles of Acetyl Produced per kilogram of catalyst per hour and moles per liter of catalyst volume per hour, for Catalyst 1 and Comparative catalysts C-1–C3 is shown in Table 3 below. As can be seen from Table 3, the platinum catalyst is nearly 30 times more active for the vapor phase carbonylation of methanol than Ni, or Pd. Comparative Example C-3 demonstrates that rates with platinum on activated carbon are comparable to those obtained with Ir on an activated carbon support. This is quite unexpected in view of Yagita and Fujimoto, *Journal of Molecular Catalysis*, 69, 191–197 (1991), discussed above.

TABLE 3

| Carbonylation | | Production Rate | |
|---|---|---|---|
| Example | Catalyst | moles/$kg_{cat}$-h | moles/$L_{cat}$-h |
| 1 | 1 (Pt) | 89 | 45 |
| C-1 | C-2 (Pd) | 3 | 1.7 |
| C-2 | C-3 (Ni) | 1.4 | 0.8 |
| C-3 | C-4 (Ir) | 93 | 53 |

Although the present invention has been shown and described in terms of the presently preferred embodiment(s), it is to be understood that various modifications and substitutions, rearrangements of parts, components and process steps can be made by those skilled in the art without departing from the novel spirit and scope of the invention.

We claim:

1. A vapor-phase carbonylation method for producing esters and carboxylic acids from reactants selected from the group consisting of lower alkyl alcohols having from 1 to 10 carbon atoms, alkane polyols having 2 to 6 carbon atoms, alkyl alkylene polyethers having 3 to 20 carbon atoms alkoxyalkanols having from 3 to 10 carbon atoms and mixtures thereof, said process comprising contacting the reactants with carbon monoxide in a carbonylation zone of a carbonylation reactor and under vapor-phase conditions with a catalyst consisting of from about 0.01 weight percent to about 10 weight percent platinum on a solid support material and a vaporous second component comprising a halide.

2. The method of claim 1 wherein said catalyst has from about 0.1 weight percent to about 2 weight percent platinum.

3. The method of claim 1 wherein said vapor-phase carbonylation has a pressure of from about 0.1 bar to 100 bars and a temperature of from about 100° C. to about 350° C.

4. The method of claim 1 wherein said vapor-phase carbonylation has a pressure of from about 1 bar to about 50 bar and a temperature of from about 150° C. to about 275° C.

5. The method of claim 1 wherein said vapor component is at least one halide selected from the group consisting of chlorine, bromine and iodine.

6. The method of claim 5 wherein said at least one halide is selected from hydrogen halides, alkyl, aryl halides having up to 12 carbon atoms, and mixtures thereof.

7. The method of claim 6 wherein said at least one halide is selected from as hydrogen iodide, gaseous hydriodic acid, methyl iodide, ethyl iodide, 1-iodopropane, 2-iodobutane, 1-iodobutane, hydrogen bromide, methyl bromide, ethyl bromide, benzyl iodide, and mixtures thereof.

8. The method of claim 6 wherein said at least one halide is selected from hydrogen iodide, methyl iodide, hydrogen bromide, methyl bromide, and mixtures thereof.

9. A vapor-phase carbonylation method for producing esters, carboxylic acids and mixtures thereof from reactants selected from the group consisting of lower alkyl alcohols having from 1 to 10 carbon atoms, alkane polyols having 2 to 6 carbon atoms, alkyl alkylene polyethers having 3 to 20 carbon atoms alkoxyalkanols having from 3 to 10 carbon atoms and mixtures thereof, said process comprising contacting said reactants and carbon monoxide with a catalyst system in a carbonylation zone; and recovering a gaseous product from the carbonylation zone, wherein said catalyst system consisting of from about 0.01 weight percent to about 10 weight percent platinum on an activated carbon support and a vaporous second component comprising a halide selected from the group consisting of chlorine, bromine and iodine.

10. The method of claim 5 wherein said at least one halide is selected from hydrogen halides, alkyl halides and aryl halides having up to 12 carbon atoms, and mixtures thereof.

11. The method of clam 9 wherein said reactant is methanol.

12. The method of claim 9 wherein said reactant is dimethyl ether.

13. A vapor-phase carbonylation method for producing acetic acid and methyl acetate comprising contacting a gaseous mixture comprising methanol and carbon monoxide with a catalyst system in a carbonylation zone; and recovering a gaseous product from the carbonylation zone wherein said catalyst system consisting of from about 0.01 weight percent to about 10 weight percent platinum on carbon support and a vaporous second component selected from hydrogen iodide, methyl iodide, hydrogen bromide, methyl bromide, and mixtures thereof.

14. The method of claim 13 wherein said catalyst has from about 0.01 weight percent to about 10 weight percent platinum.

15. The method of claim 13 wherein said at least one halide is selected from hydrogen iodide, methyl iodide, hydrogen bromide, methyl bromide, and mixtures thereof.

* * * * *